United States Patent
Häusler

(10) Patent No.: US 9,091,536 B2
(45) Date of Patent: Jul. 28, 2015

(54) METHOD AND DEVICE FOR THREE-DIMENSIONAL SURFACE DETECTION WITH A DYNAMIC REFERENCE FRAME

(75) Inventor: Gerd Häusler, Erlangen (DE)

(73) Assignee: Dentsply International Inc., York, PA (US)

(*) Notice: Subject to any disclaimer, the term of this patent is extended or adjusted under 35 U.S.C. 154(b) by 673 days.

(21) Appl. No.: 12/791,461

(22) Filed: Jun. 1, 2010

(65) Prior Publication Data

US 2010/0303341 A1   Dec. 2, 2010

Related U.S. Application Data

(60) Provisional application No. 61/182,927, filed on Jun. 1, 2009.

(51) Int. Cl.
  G06K 9/00     (2006.01)
  G06T 15/00    (2011.01)
  G01C 3/14     (2006.01)
  G01B 11/25    (2006.01)
  (Continued)

(52) U.S. Cl.
  CPC .......... *G01B 11/2513* (2013.01); *A61B 5/0062* (2013.01); *A61B 5/1077* (2013.01); *A61B 5/1079* (2013.01); *G01B 11/2522* (2013.01); *G01B 11/2531* (2013.01); *G06T 7/0028* (2013.01); *G06T 7/0057* (2013.01); *A61B 5/4547* (2013.01); *G06T 2207/10016* (2013.01); *G06T 2207/10028* (2013.01); *G06T 2207/30036* (2013.01)

(58) Field of Classification Search
  None
  See application file for complete search history.

(56) References Cited

U.S. PATENT DOCUMENTS 4,825,263 A * 4/1989 Desjardins et al. ........... 356/603
5,003,166 A * 3/1991 Girod ......................... 250/201.4
(Continued)

FOREIGN PATENT DOCUMENTS

EP   1355127 A2    10/2003
WO   9303579 A1    2/1993
WO   2009063087 A2 5/2009

OTHER PUBLICATIONS

Reich et al., "3-D shape measurement of complex objects by combining photogrammetry and fringe projection", Opt. Eng. 39(1) 224-231 (Jan. 2000).*

(Continued)

*Primary Examiner* — Randolph I Chu
(74) *Attorney, Agent, or Firm* — Laurence A. Greenberg; Werner H. Stemer; Ralph E. Locher

(57) ABSTRACT

The surface shape of a three-dimensional object is acquired with an optical sensor. The sensor, which has a projection device and a camera, is configured to generate three-dimensional data from a single exposure, and the sensor is moved relative to the three-dimensional object, or vice versa. A pattern is projected onto the three-dimensional object and a sequence of overlapping images of the projected pattern is recorded with the camera. A sequence of 3D data sets is determined from the recorded images and a registration is effected between subsequently obtained 3D data sets. This enables the sensor to be moved freely about the object, or vice versa, without tracking their relative position, and to determine a surface shape of the three-dimensional object on the fly.

19 Claims, 11 Drawing Sheets

(51) Int. Cl.
*A61B 5/00* (2006.01)
*A61B 5/107* (2006.01)
*G06T 7/00* (2006.01)

(56) References Cited

U.S. PATENT DOCUMENTS

| | | | | |
|---|---|---|---|---|
| 5,231,678 | A * | 7/1993 | Takatori et al. | 382/154 |
| 6,128,086 | A | 10/2000 | Fowler et al. | |
| 6,373,963 | B1 * | 4/2002 | Demers et al. | 382/108 |
| 7,164,789 | B2 * | 1/2007 | Chen et al. | 382/154 |
| 7,313,264 | B2 * | 12/2007 | Crampton | 382/154 |
| 7,672,504 | B2 * | 3/2010 | Childers | 382/154 |
| 2002/0191834 | A1 * | 12/2002 | Fishbaine | 382/150 |
| 2004/0076313 | A1 * | 4/2004 | Bronstein et al. | 382/118 |
| 2006/0192925 | A1 * | 8/2006 | Chang | 353/94 |
| 2007/0081718 | A1 | 4/2007 | Rubbert et al. | |
| 2008/0101688 | A1 * | 5/2008 | Quadling et al. | 382/154 |
| 2009/0274350 | A1 * | 11/2009 | Pavlovskaia et al. | 382/128 |
| 2010/0000383 | A1 * | 1/2010 | Koos et al. | 83/22 |
| 2010/0209002 | A1 | 8/2010 | Thiel et al. | |
| 2011/0058023 | A1 * | 3/2011 | Boles et al. | 348/46 |
| 2011/0081072 | A1 * | 4/2011 | Kawasaki et al. | 382/154 |
| 2011/0158508 | A1 * | 6/2011 | Shpunt et al. | 382/154 |

OTHER PUBLICATIONS

Sato et al., "Three-Dimensional Shape Reconstruction by Active Rangefinder", IEEE, 1993, 142-147.*
Hainich et al., DLP-Based 3D Metrology by Structured Light or Projected Fringe Technology for Life Sciences and Industrial Metrology, Proc. of SPIE vol. 7210, 2009, 1-12.*
Proesmans et al., One-Shot Active 3D Shape Acquisition, 1996, IEEE, 336-340.*
Sato et al., Shape Measurement of Curved Objects Using Multiple Slit-Ray Projections, IEEE Transactions on Pattern Analysis and Machine Intelligence, vol. PAMI-4, No. 6, Nov. 1982, 641-646.*
International Search Report dated Dec. 10, 2010.

* cited by examiner

METHOD AND DEVICE FOR THREE-DIMENSIONAL SURFACE DETECTION WITH A DYNAMIC REFERENCE FRAME

CROSS-REFERENCE TO RELATED APPLICATION

This application claims the benefit, under 35 U.S.C. §119 (e), of my copending provisional patent application 61/182,927, dated Jun. 1, 2009. The earlier application is herewith incorporated by reference in its entirety.

BACKGROUND OF THE INVENTION

1. Field of the Invention

The invention relates to a method and a device for scanning and digitizing three-dimensional surfaces. The invention is applicable, in particular, to any implementation in which a surface in three-dimensional space may be digitally acquired and processed.

2. Description of the Related Art

Most existing optical 3D sensors require the acquisition of multiple 2D camera images in order to obtain 3D data. The most common technique is the so-called "fringe projection" technique [ref M. Halioua, H. Liu, V. Srinivasan, "Automated phase-measuring profilometry of 3-D diffuse objects," in Appl. Opt. 23 (1984) 3105-3108], which is widely commercially available, for example the Face Scan sensor by 3D-Shape GmbH, Erlangen, Germany. A projector projects a fringe pattern onto the object. One or more cameras observe the object surface. In general, at least three fringe patterns have to be projected in a sequence resulting in at least three 2D-raw images. For better accuracy, most fringe projection sensors take even more raw images. During the time it takes the series of raw images, the object and the sensor have to stand still, which makes the sensor not well adapted, when relative motion between object and sensor is involved.

In many applications, the object has a complicated shape, so the acquisition of the 3D topography cannot be achieved from a single observation direction. The sensor has to take data from different directions which then are registered. This procedure needs a stop and go movement of the sensor, which makes the measurement quite uncomfortable, even more so because only after the time consuming registration of the different views the user will know if there are parts of the object missing. Nevertheless, the fringe projection principle is widely used, as it supplies an acquisition of up to 1 Mio high quality data points within each viewing direction.

Using an additional modality such as color, it is principally possible to make a sensor that needs only one single raw (color) image to acquire a complete 3D topography [ref G. Hausler and D. Ritter, "Parallel 3D-sensing by color-coded triangulation," in Appl. Opt. 32, No 35 (1993) 7164-7169]. The achievable quality of the data and the technical costs however, make the sensor not yet competitive.

There exist other options to achieve a "single shot 3D sensor." However, those sensors principally cannot deliver a complete set of 3D data. The simplest single-shot sensor is based on light sectioning triangulation [G. Häusler and W. Heckel, "Light sectioning with large depth and high resolution," in Appl. Opt. 27 (1988) 5165-5169]. Instead of projecting a full field fringe pattern, only one single line (or a couple of lines) is projected onto the object surface. So from one single raw image one can acquire one 3D line profile, or if several lines are projected, one can acquire several 3D line profiles. Between the line profiles ("3D sections"), no data are available. We call such 3D data "sparse."

To summarize, we have the motion sensitive fringe projection systems that acquire complete 3D data, and the motion robust light sectioning sensors that deliver just sparse 3D data. Our goal is a new sensor that will use the single shot principle but will nevertheless deliver complete and high quality 3D data of the object surface.

To a certain extent, there are existing solutions, for example the T-Scan 3 sensor from Steinbichler Optotechnik GmbH, 83115 Neubeuern, Germany. That sensor can be hand guided over the object surface to generate a more or less complete 3D surface reconstruction. However, the sensor needs an additional tracking system, realized by a photogrammetric camera system. The sensor uses only one-line laser triangulation, which makes it difficult to get complete and very accurate data. The necessity to track the sensor makes a completely free motion difficult, because the tracking field of view must not be obscured by the person who moves the sensor.

The concept of acquiring a surface by moving the sensor and subsequently register 3D data is realized as well by the so called "3D from motion" principle, described, for example by C. Tomasi and T. Kanade: "Shape and Motion from Image Streams under Orthography: a Factorization Method," in International Journal on Computer Vision, 9(2), 137-154, 1992. A camera is moved and takes different 2D raw images, and from the extracted corresponding points in different views, a 3D reconstruction can be achieved. Shape from motion commonly is a passive method, with no projected markers, so it is difficult to obtain a complete surface reconstruction.

There are increasing demands to use the technology of 3D acquisition, for example, in the field of intraoral sensors. Most existing intraoral sensors require the acquisition of multiple 2D camera images in order to obtain 3D data. A most prominent sensor is the "Cerec" sensor by Sirona. It is based on the principle of "fringe projection." After an acquisition of at least three 2D images a 3D view can be obtained. Within the acquisition period (longer than 100 ms), the sensor and the object have to stand still. The measurement principle of the sensor, which requires several camera images in order to generate 3D data, is cumbersome and spurious, because relative motion between sensor and object under test during acquisition is not permitted.

Another state-of-the-art sensor is "directScan" by Hint-Els. It combines fringe projection with phase correlation. In a first step, two series of orthogonal stripe patterns, each series consisting of at least three images, are projected, one after the other, onto the surface to be acquired. From each of the two series of captured camera images, a phase evaluation is performed. In a second step, all resulting pairs of phase values are correlated in order to determine even a more robust and more precise single phase value for each camera pixel. From this information, a set of 3D points is calculated. Hence, it requires an acquisition of multiple 2D images in order to generate a 3D view. Within the acquisition time window (about 200 ms), the sensor and the object are not allowed to move, making a motion-robust measurement impossible.

A variety of other sensors are in use. One such sensor is "iTero" by Cadent which is based on "parallel confocal imaging." 100,000 points of laser lightning at 300 focal depths are employed, yielding a lateral resolution of 50 μm. During the acquisition at these 300 focal depths (the scanning through different z-positions is necessary in order to generate one 3D view, taking about 300 ms), the sensor does not allow motion. The necessity of an acquisition of multiple images, again, renders the sensor cumbersome in its use. It is especially disadvantageous that the sensor must be moved to pre-determined positions, thus rendering free-hand guidance during the acquisition impossible.

The prior art system "Lava" by 3M Espe employs the so-called "active wavefront sampling" principle. An off-axis rotating aperture generates a circular pattern, rotating at the object surface. From the diameter of this rotation the defocusing and the distance of the considered area can be determined.

One prior art sensor enables a motion-robust measurement of objects. It is the "SureSmile" sensor by OraMetrix. The OraMetrix system projects one type of pattern. It is based on active triangulation and on a single-shot principle: One 2D camera image already delivers 3D data (roughly 60×60 3D points per 3D view). It acquires about 6 images/second. The application is not the complete acquisition of a surface in space and the system cannot provide the best possible measuring uncertainty.

BRIEF SUMMARY OF THE INVENTION

It is accordingly an object of the invention to provide a method and device for 3D acquisition which overcome the above-mentioned disadvantages of the heretofore-known devices and methods of this general type and which provide for a motion-robust, freely movable low-cost, and scalable optical 3D sensor enabling a simple and robust acquisition of object surfaces "on the fly."

With the foregoing and other objects in view there is provided, in accordance with the invention, a method of acquiring surface shape information of a three-dimensional object. The method comprises:

providing an optical sensor configured to generate three-dimensional data from a single exposure, the sensor having a projection device and a camera;

causing a relative movement between the sensor and the three-dimensional object;

projecting a pattern with the projection device onto the three-dimensional object and recording a sequence of at least partially overlapping images of the projected pattern with the camera;

determining a sequence of 3D data sets from the recorded images;

performing a registration between subsequently obtained 3D data sets; and determining a surface shape of the three-dimensional object.

Implementations of the invention range from intraoral measurement of teeth to the 3D acquisition of larger objects such as human body, crime scene acquisition, the interior of rooms or even buildings, and quality testing in manufacturing assemblies. Since the sensor allows to be moved over the object surface, it enables the acquisition of the 3D topography of complex objects by moving the sensor freely around the object. Conversely, as described, it is also possible to move the object relative to the sensor (or, even, to move the sensor and the object).

It is a further object to allow the user to see in real time the already acquired 3D data as a visualization of the already acquired parts of the object. Thus, the user should be able to move the sensor in a way that not yet acquired parts of the objects can be acquired in an interactive manner.

Another application that exploits again the motion robustness of the sensor is the option, to move the sensor by a robot or by using a translation stage along the surface to be acquired. So even larger objects, such as cars or the interior of rooms, can be measured with a small field sensor. The motion robustness allows as well that the object may be moved against the sensor. This is often unavoidable, for medical applications. Another application is the acquisition of objects that move relatively to the sensor, such as work pieces at a conveyor belt.

The new sensor, described herein exploits triangulation by line projection. The basic principle is well known, one description is for example published in G. Häusler and W. Heckel: "Light sectioning with large depth and high resolution," in Appl. Opt. 27 (1988) 5165-5169. A series of thin bright lines is projected onto the object surface. The surface is observed by a camera. The axis of the projection lens and the axis of the camera enclose the angle of triangulation. The two axes span a so-called triangulation plane. From the deformation of the observed fringes, profiles $z(x,y)$ of the surface can be evaluated via some calibration procedure. If we project N lines, we can acquire N profiles within one camera image. The surface area between the lines is inaccessible, so the 3D data are sparse. The present invention is configured to overcome that problem as well.

In accordance with an added feature of the invention, the method further comprises:

determining a first 3D data set from the first image recorded by the camera immediately following the recording step;

subsequently projecting a further pattern with the projection device and recording a second image with the camera and immediately determining a second 3D data set from the second image recorded by the camera;

performing a registration between the first 3D data and the second 3D data;

subsequently recording further images and determining further 3D data, and performing registration between the further 3D data set and a previously acquired 3D data set, or several or all previously acquired 3D data sets;

for determining the surface shape of the three-dimensional object in real time as the sensor and the object are moved relative to one another.

In accordance with an added feature of the invention, the pattern has a plurality of first lines extending in a given direction and a plurality of second lines extending in a different direction traversing the first lines. Advantageously, the pattern is formed by projecting a first pattern with the first lines and recording an image with the camera, and subsequently projecting a second pattern with the second lines and recording an image with the camera, and continuing with an alternating projection and recordation of the first and second patterns.

The first lines and the second lines are perpendicular to one another in a shape of a grid pattern. When the patterns are projected alternatingly, of course, the "grid" is formed only with a time offset. When the grid pattern is projected in a single projection, the points of intersection or crossing points are directly projected.

In accordance with an added feature of the invention, the method comprises continuing the projection, recording, and registration steps on the fly to form a point cloud representing the surface shape of the object and displaying the surface shape virtually in real time. Advantageously, the system allows adapting a projection and exposure time period to a relative speed between the sensor and the object and to avoid a motion blur of the resulting three-dimensional data.

In accordance with the invention, the method comprises using sparse three-dimensional data in order to avoid ambiguity and false data. In general, so-called single-shot sensors acquire "sparse" data. Increasing the number of lines by too much renders the data less sparse and the lines can no longer be uniquely identified without great difficulty.

In accordance with a further feature of the invention, the method comprises:

moving the sensor along a suitable path about the object and acquiring a multiplicity of exposures, and thereby adjusting the speed of motion and the frame rate so that adjacent pictures have significant overlap;

calculating a series of sparse 3D data of the object from the exposures;

registering each of the sets of 3D data with previously acquired 3D data sets and obtaining a substantially complete set of 3D data of the object;

displaying a representation of the 3D data to a user in real time in order to prompt the user to cover as of yet non-covered areas of the surface of the object.

It is also possible, in furtherance of the registration step, to reduce and correct registration errors by reconstructing a path of the sensor, by resection, and by finding registration errors via a deviation of the reconstructed sensor path from a smooth interpolated curve.

According to the novel invention the measurement principle of the sensor requires one camera image in order to generate 3D data. The data are sparse, but in combination with taking a series of images while the sensor is moved along the surface, and by registration of the series of 3D data, the sensor principle provides for the advantageous system according to the invention.

The data are sparse, but relative motion between the sensor and the object under test is permitted. It is centrally important that an optimal embodiment in the context of the invention that allows for best registration, the novel sensor uses two different patterns that are projected intermittently. The patterns are alternatingly projected orthogonal patterns, each yielding 3D data.

With the above and other objects in view there is also provided, in accordance with the invention, a sensor for acquiring data representing a surface of a three-dimensional object, comprising:

a projection device having a light source and optics for projecting an optical pattern onto the surface of the three-dimensional object, the projection device having an optical axis;

a digital camera for recording an image of the optical pattern projected onto the surface of the three-dimensional object, the digital camera having a given optical axis;

the optical axis of the digital camera and the optical axis of the projection device enclosing a given angle and defining a triangulation plane; and a control unit connected to and synchronizing the projection device and the digital camera and causing the camera to record a sequence of mutually overlapping images of the optical pattern sequentially projected onto the surface of the object.

In accordance with yet a further feature of the invention, the digital camera is a monochromatic camera.

In accordance with an added feature of the invention, the projection device comprises two projectors each having a light source, a condenser, a pattern slide, and projection optics defining an optical axis enclosing an angle with the optical axis of the camera and each defining a triangulation plane. Advantageously, the two projectors project mutually perpendicular patterns, the camera records the projected patterns of the two projectors in alteration, and the triangulation planes defined by the camera and the two projectors, respectively, are perpendicular to one another.

In an alternative embodiment of the invention, the projection device comprises a single projector configured to project mutually different patterns and the camera records the projection of the different patterns in alteration. It is a further alternative embodiment to project a single "grid" pattern. The resulting projector, and the sensor, is quite inexpensive and simple because no electronic projection pattern switching is required.

Advantageously, the sensor is a handheld sensor for movement about six degrees of freedom that enables the acquisition of complex surfaces. It is preferred to provide an output connection enabling connection to a display device for displaying an acquisition result virtually in real time.

The invention described herein presents a low cost and easy-to-handle sensor which enables a freely movable, for example hand-guided, motion-robust acquisition of object surfaces. The so-called "Flying Triangulation" sensor combines a simple sensor principle with sophisticated algorithms. It is based on "active triangulation": A system synchronizes the signal from a camera and either two projection units (P1 and P2), with patterns projected alternately from P1 and P2 onto the object under test, or a single projector with two or more alternating patterns projected onto the object, or a single projector with a single pattern (e.g., a grid) projected onto the object, in order to obtain a series of 2D camera images.

While the following text may refer to two projection units, the single projection unit with different projection patterns, or a single cross-pattern, should be understood as being equivalent, although less accurate, as explained in the following:

The two projectors span two perpendicular directions of triangulation and project line patterns that are perpendicular to each other. This feature is crucial for an effective and accurate registration. Each camera image yields a (sparse) 3D view. A sequence of those sparse 3D views is acquired as a film. By aligning (register) the 3D views to each other the complete object surface is obtained. The alignment happens during the acquisition of the series of views. Accordingly, the user of the sensor is able to see a visualization of the object surface in 3D space, in real time. The user can also observe missing areas and will be able to revisit those areas during the acquisition process, so as to fully acquire and cover the entire surface of interest.

Once more in summary, the surface shape of a three-dimensional object is acquired with an optical sensor. The sensor, which has a projection device and a camera, is configured to generate three-dimensional data from a single exposure, and the sensor is moved relative to the three-dimensional object, or vice versa. A pattern is projected onto the three-dimensional object and a sequence of overlapping images of the projected pattern is recorded with the camera. A sequence of 3D data sets is determined from the recorded images and a registration is effected between subsequently obtained 3D data sets. This enables the sensor to be moved freely about the object, or vice versa, without tracking their relative position, and to determine a surface shape of the three-dimensional object on the fly Other features which are considered as characteristic for the invention are set forth in the appended claims.

Although the invention is illustrated and described herein as embodied in a method and device for three-dimensional surface detection with a fully dynamic reference frame, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best under-

DETAILED DESCRIPTION OF THE INVENTION

Figure 1:
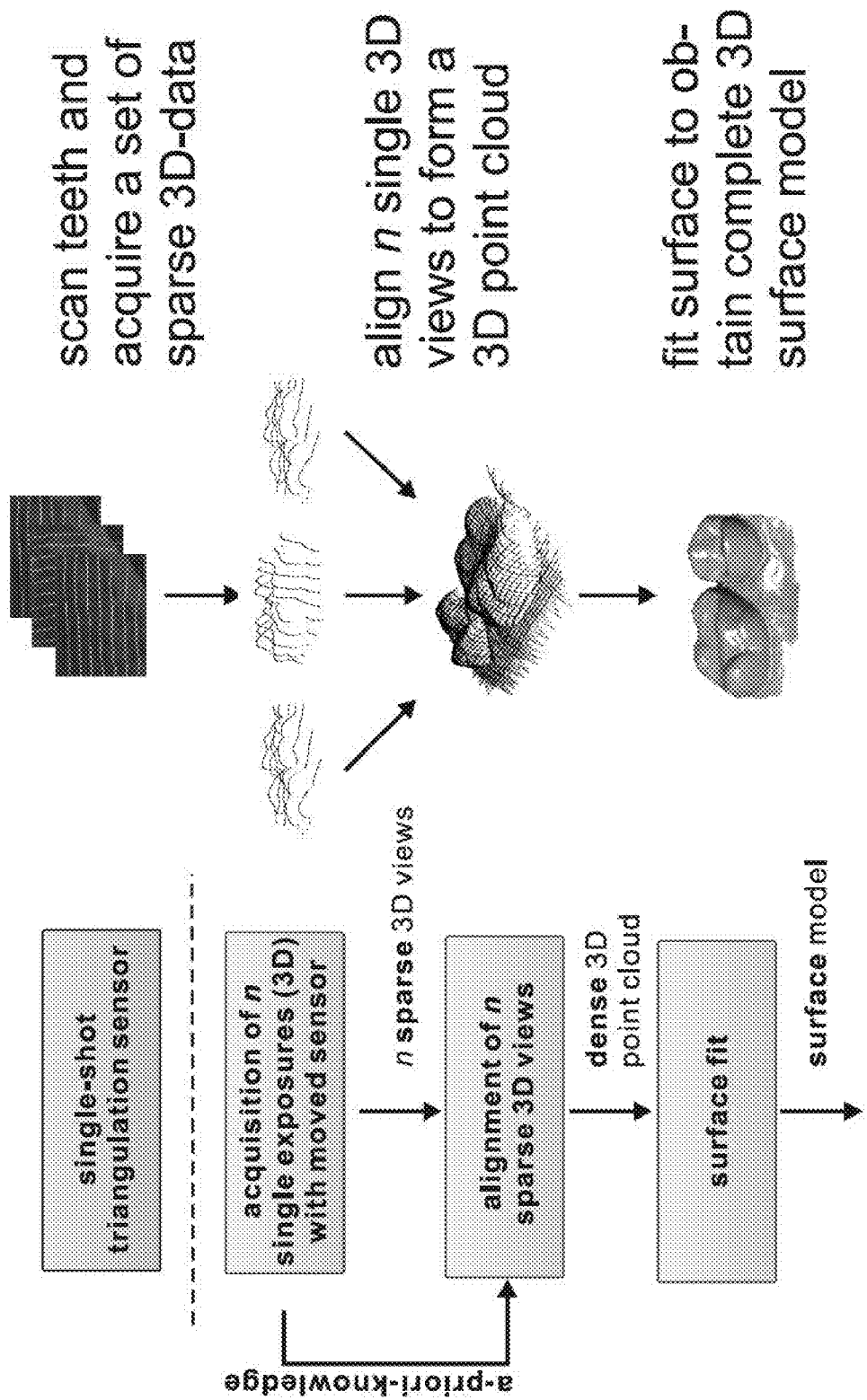
FIG. 1 is a flow diagram illustrating the work flow of the flying triangulation principle according to the invention.
Figure 2:
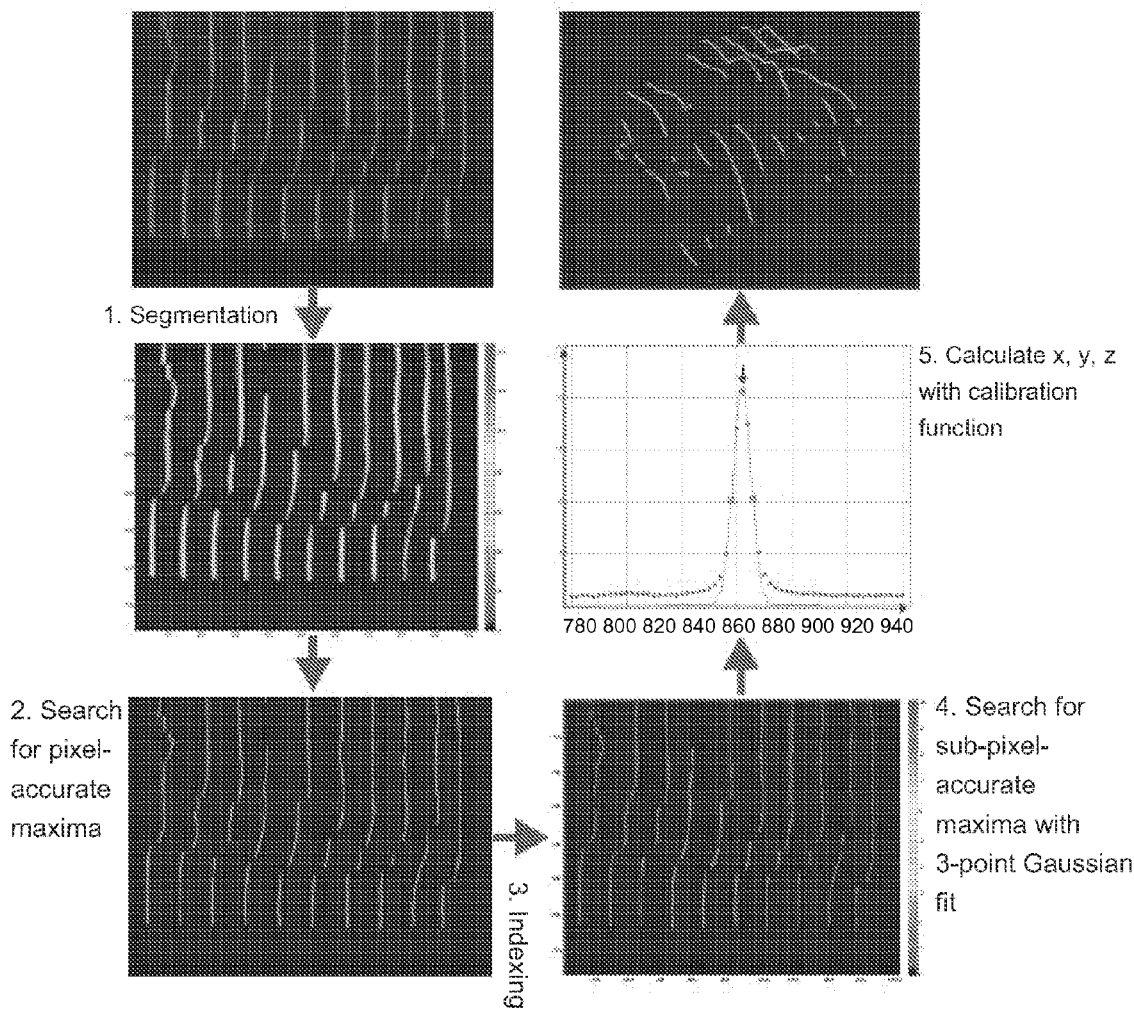
FIG. 2 is an image sequence illustrating the interpretive calculation for a 3D view display.

Referring now to the figures of the drawing in detail and first, particularly, to FIG. 1 thereof, there is seen a flow chart with a workflow sequence of the flying triangulation principle with reference to the acquisition of dental information. In a first step, a geometrical calibration of the sensor is performed and the parameters are determined that are necessary to obtain 3D data from the camera images. Beginning with the first acquired camera image, an algorithm calculates a 3D view from each 2D camera image. That result is displayed in FIG. 2.

Initially, a preview of the unregistered (i.e., non-aligned) 3D data is displayed live to the user (e.g., two to four 3D data sets, not the camera images), in order to allow the proper positioning of the sensor. In the alternative, it is also possible to display a camera image (or video) in order for the user to immediately see the proper positioning of the sensor. After initiating the measuring sequence, an indexing module determines the correct labels of the line pieces of the observed line pattern by employing signal processing methods. In order to avoid incorrect labeling, the line pattern is chosen in a way to ensure that the image of the line with the index k, l, . . . can occur only within a predetermined area labeled k, l, . . . in the camera image, see FIG. 3 for reference.

If the object lies outside the measurement volume, the indexing leads to false results. This incorrect indexing can be avoided by assuring that such outside placement of the object can be recognized. This may be done either by way of a hardware solution, i.e., an additional optical or ultrasound sensor that detects an object exceeding the measurement range, or by using a-priori knowledge of the object that is being scanned. With such an algorithmic solution an indexing error can be detected by unwrapping.

Then, a sub-pixel module determines the sub-pixel precise positions of the intensity maxima of each signal for each line and calculates the corresponding highly accurate 3D points.

In a final step, the data is loaded into the registration and visualization software to align the data and to visualize the result of the point cloud of the complete object surface thus obtained.

The following text describes details of how the sensor parameters may be configured.

The main source of noise for an active triangulation sensor is speckle noise. The corresponding depth noise $\delta z$ is given by Eq. (1):

$$\delta z = \frac{C}{2\pi} \frac{\lambda}{\sin u_{obs} \sin \theta}, \quad (1)$$

where C is the speckle contrast, $\lambda$ is the mean wave length of the light source, the term $\sin u_{obs}$ represents the observation aperture, and $\theta$ is the triangulation angle. By choosing a large observation aperture $\sin u_{obs}$ or by choosing a large triangulation angle $\theta$ the measurement uncertainty of the sensor can be reduced. However, most of these parameters are pre-determined by the application: The triangulation angle has to be small in order to minimize shading effects; commonly, $\theta\sim7°$ is chosen for dental measurement. The observation aperture determines the depth of field given by Eq. (2)

$$\delta z_{Rayleigh} = \frac{\lambda}{\sin^2 u_{obs}}, \quad (2)$$

with parameters as described above. For intraoral measurements, a depth of field of 15 mm is appropriate, which requires a small observation aperture of less than 0.01. A small observation aperture implies a large depth of field but also high speckle noise, according to Eq. (1). Since the observation aperture and the triangulation angle cannot be chosen freely but have to be adapted to the application, the speckle contrast C is the only parameter that can be optimized to reduce the speckle noise.

Speckle noise may be reduced, in accordance with the invention by:

spraying the surfaces with material such as titanium dioxide that causes diffuse volume scattering, (also reduces measuring errors on teeth) in combination with employing (bright) white-light LEDs as light sources for the pattern projection. The LEDs display a coherence length that is shorter than the thickness of the spray layer. This reduces the speckle contrast C, and thus provides minimal measurement uncertainty. Experiments show that by this method the depth uncertainty due to speckle noise can be reduced in a way so as to achieve a great depth of field of about 15 mm and at the same time a measuring uncertainty of less than 30 μm within the total measuring volume in a single 3D view.

The projection device displays a projection aperture $\sin u_{proj}$ and an illumination aperture $\sin u_{ill}$. The projection aperture is chosen as large as possible and as small as necessary. According to the invention, the projection aperture and the illumination aperture of the pattern projectors, as well as the line width of the projected lines, are optimized for a) large depth of field, b) and low spatial coherence, c) as well for optimal brightness, d) and for optimal measuring uncertainty.

Figure 4:
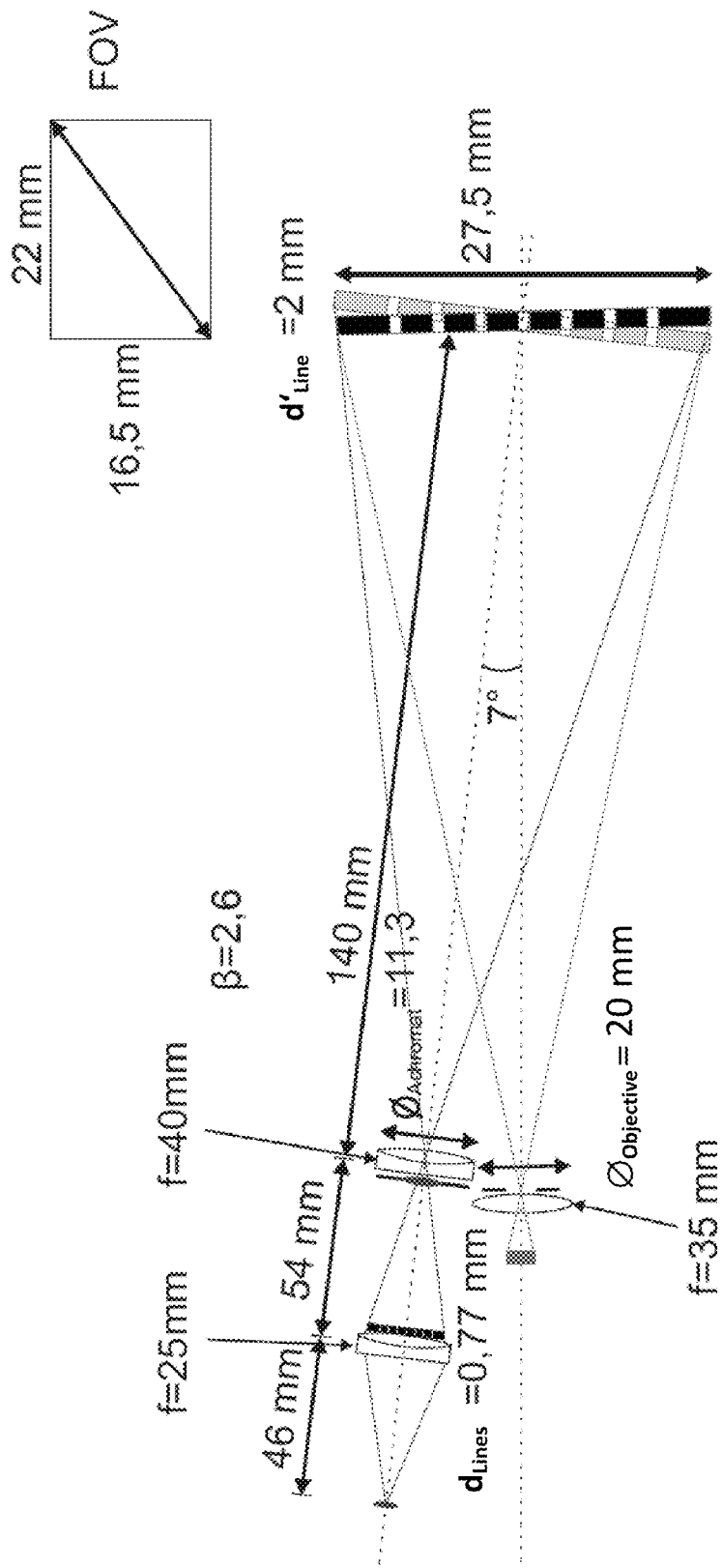
FIG. 4 is a diagrammatic sketch of a miniaturized sensor according to the invention.

The choice of the line width on the slide and the means to achieve the proper line width on the object over the entire depth of field, with low speckle contrast and with high image illumination, is effected as follows, according to the invention: The projection aperture is chosen in a way that the depth of field of the projection corresponds to the application (e.g., 15 mm for dental measurements; 300 mm for measurement of, say, a human body). The illumination aperture is given by the image of the light source in the projection lens and the projection distance. Reference is had to FIG. 4, where the projection distance is shown to be approximately 140 mm.

According to the invention, the illumination aperture is as large as possible, which means that the image of the light source fills the full aperture stop of the projection lens, and it should not be smaller than the observation aperture. This feature reduces the speckle contrast, compared to a smaller illumination aperture.

This feature further enables the maximum achievable illumination with a given light source. The illumination aperture is chosen in a way to achieve an optimal width of the projected lines: The width of the projected lines is optimal when the width of the line image at the camera target is about 3-5 pixels. Then the sub-pixel interpolation of the camera line profile yields the lowest possible depth error. At the same time, the lateral resolution on the object surface is optimal. For dental measurements, the lateral resolution should be in the range of 30-80 μm.

The sensor is calibrated employing a model-independent calibration method. Two calibration steps are required:

First, a calibration of the z-coordinate $$z=K_z(i,j,h),$$

where i and j index the pixel coordinates of the camera CCD-chip, h=h(i,j) is the uncalibrated height value, and $K_z$ is the calibration function which needs to be determined. For this purpose, N camera images of each of the line patterns projected onto a planar background are acquired by taking one image in the front of the measurement volume, then shifting the plane by a fixed Δz-offset, taking the second image, etc, until an image at the end of the measurement depth is acquired. For each pixel pair (i,j), a z-calibration function ($3^{rd}$-order polynomial) through the measurement volume is determined.

Second, a lateral calibration of the x/y-coordinates building on the z-calibration:

$$x=K_x(i,j,z),$$

$$y=K_y(i,j,z),$$

where $K_x$ and $K_y$ describe the (independent) calibration functions for the x- and y-calibration, respectively. For this purpose, M camera images of a calibration plate consisting of n×m markers are acquired, again by moving the plate by a fixed Δz-offset through the measurement volume. The positions of the markers are determined and a calibration function ($3^{rd}$-order polynomial) is calculated which maps each observed marker position to its corresponding target value.

A "movie" of 2D images is acquired. An acquisition module captures the current camera image and saves it to the computer. From the movie a series of (sparse) 3D views are generated by employing the indexing module and the sub-pixel module and the calibration functions resulting from the calibration method described above. The indexing module and the subpixel module together represent the so-called 3D profile module.

In order to obtain a complete, dense 3D point cloud of the object surface, all 3D views, each approximately consisting of 7000 3D points, in a certain embodiment, need to be aligned with each other. This is referred to as "registration."

Registration of sparse 3D data which lie relatively close to each other, because the relative movement between two exposures is small, is effected as follows: Two steps are necessary, first a coarse registration, followed by a fine registration. The key concept underlying the coarse registration is to project two consecutive 3D views onto each other and moving them relative to each other until their distance-based error function is minimized. The resulting transformation parameters are used as the start values for the following fine registration. Here, the best position of the two consecutive 3D views is iteratively determined.

An alternative coarse and fine registration approach would be based on modules which can be independently called (in parallel). In an adder module, the next 3D view is consecutively aligned to the already aligned 3D views.

The real-time coarse registration is a very advantageous process of the invention. It is possible to display the results visually even before the registration errors have been minimized. This allows visualization so that the user may immediately guide the sensor to those locations that have not yet been measured. Depending on the capacity of the processor, the fine registration for achieving the exact surface may be effected parallel to the coarse registration or subsequently to the measurement and coarse registration. The sensor according to the invention renders it possible to immediately and in real-time show the user what is being measured. This is possible only because the sparse data required by the invention do not unnecessarily overload the processor during the registration process, which would be the case if one were to measure and calculate, say, one million points at the same time.

Visualization is effected by calculating the normals at the points of intersection. Along the lines outside the points of intersection, we only know the normal component in the section plane. The normal component that is perpendicular to the section plane is not known. That component, however, is interpolated from the normals at the points of intersection. The surface can then be visualized with the aid of these components. We refer to this as standard rendering or shading: a virtual light source at a predeterminable location, the object normal, and the point of view (i.e., the viewing direction) are calculated such that a photorealistic image of the object surface may be presented to the user. Further, the increasing density during the measurement causes the visualized point cloud to look like a closed surface after only a very brief time during the measurement. It is, furthermore, easily possible, to display the point cloud in a fixed position and orientation of the object, or the object can be displayed as if viewed from the camera.

The photorealistic display, which, first, is shown in black and white, is possible in a simple manner, because the normals in the points of intersection are known. It is not easily and failure-free possible to visualize the surface with other sensors that only deliver non-connected point clouds. As mentioned further below, it is also possible to provide color rendering and color display, which, in general, is preferred by most users.

From the previously aligned views, transformation parameters for the aligning (registration) are estimated, that means: we determine the motion parameters of the sensor which are available by resection and make a guess by extrapolation of these motion parameters, about the new position and orientation of the sensor. This procedure makes the next step, which is an iterative step, converge faster. The step is a so-called iterative closest point (ICP) algorithm, as described by P. Besl and N. McKay: "A method for Registration of 3-D Shapes," in IEEE PAMI, 14(2) (1992) 239-256. The ICP algorithm used here is especially adapted to sparse 3D data.

A multiregistration module re-registers 3D views in multiple view packages in order to reduce the global error.

A spacecurve module detects and eliminates registration outliers. The (known) sensor path is reconstructed for this purpose. Commonly, the sensor moves along a smooth curve. If there are outliers of the registration, this would cause an apparent sudden local change in the reconstructed sensor path. According to the invention, we skip those exposures and do not use them for registration. Since there are so many exposures, the data contains a considerable amount of redundancy to remove errors or to smooth out noise.

Registration of 3D data sets with this sensor concept is more accurate than registering 2D data, since the sensor has a high depth resolution of <30 µm. Therefore the registration is done with 3D data sets to obtain accurate and efficient registration results. This is done by using sequentially adjacent 3D data sets, one generated with a horizontal line pattern and the other with a vertical line pattern. The registration takes place by iterative movement of one of the 3D data sets relative to the other until a minimum distance between all crossing points between the traversing vertical and the horizontal line pattern is reached. Ideally the different line patterns are perpendicular to each other.

The final mode performs a global optimization of the registration parameters. For this purpose, weights are determined for overlapping 3D views, in order to find an optimal registration result.

Should the registration process performed with the adder module fail, there is provided a fallback method. It is based on the model of a table-position on a hilly landscape. The basic concept may be explained with a four-legged table on an uneven surface: a table with four legs will not stand stable everywhere on an uneven surface (e.g., hilly landscape). We look for a position of the table where all four feet are at the ground. The feet of the table are represented by the crossing points of light sections from subsequent exposures (or from other exposures). The registration procedure works principally by moving the table around while determining the distance of the fourth leg to the ground. By iteration we find the position where all four legs are hitting the ground (within a given minimal distance). This corresponds to the correct alignment of the two patterns.

A segment module aligns different segments of a point cloud to a single one. For this purpose, a hierarchic data structure enables a fast search for neighbored 3D points. In combination with the normals, a coarse registration is possible, e.g. by detecting and mapping corresponding local surface features onto each other.

Figure 3:
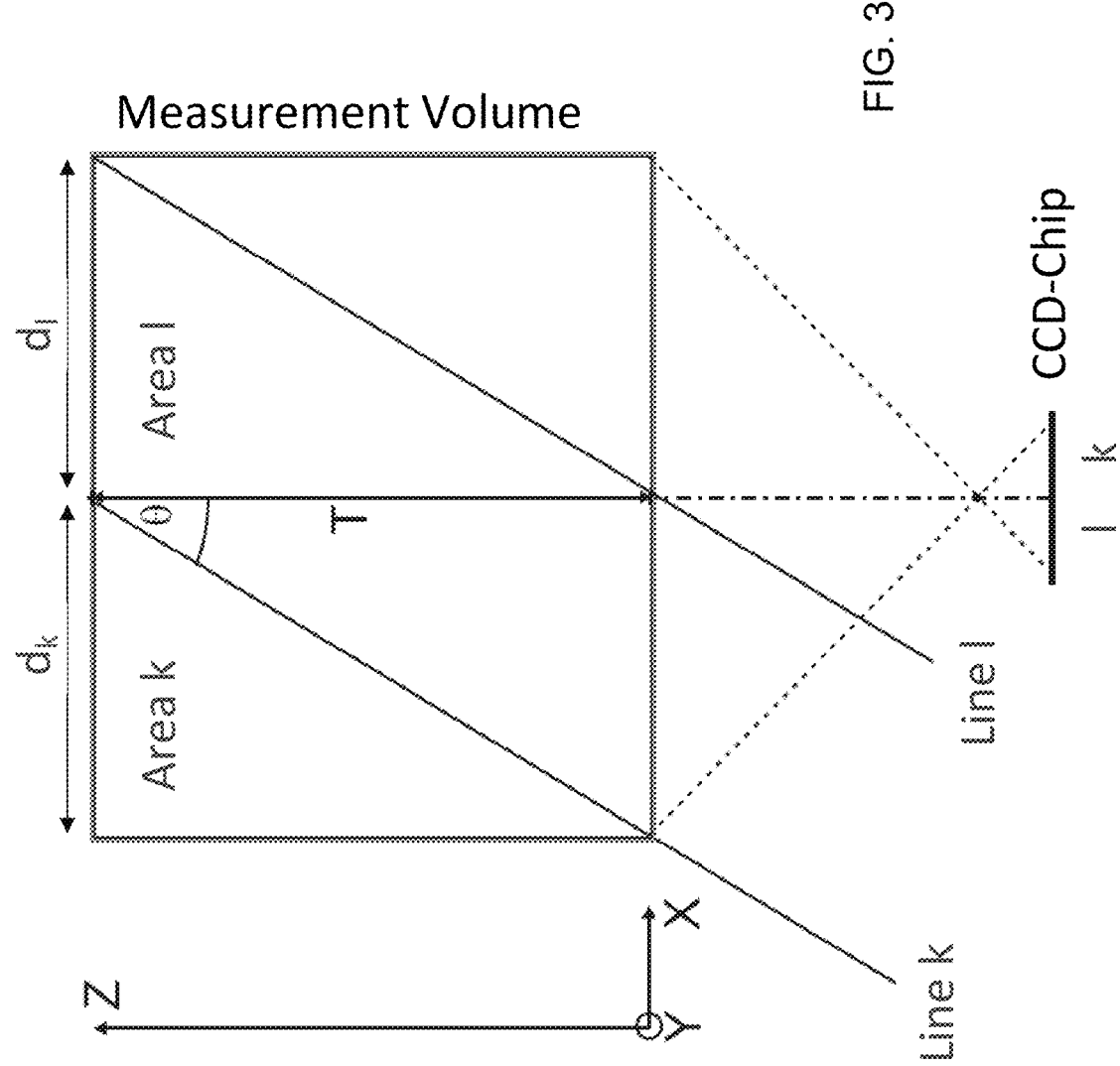
FIG. 3 illustrates the system for indexing the reference between the object and the camera chip array.
Figure 5:
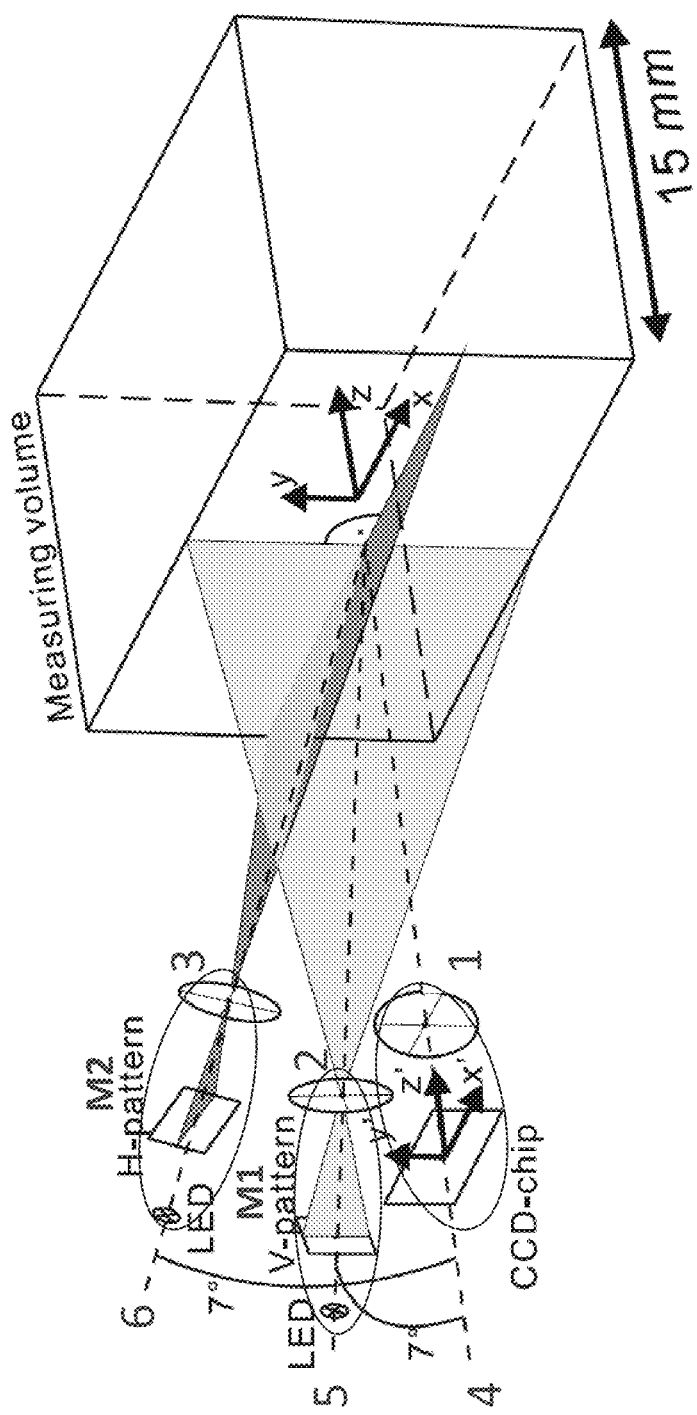
FIG. 5 is a diagrammatic illustration of an exemplary embodiment of a 3D sensor according to the invention.
Figure 6B:
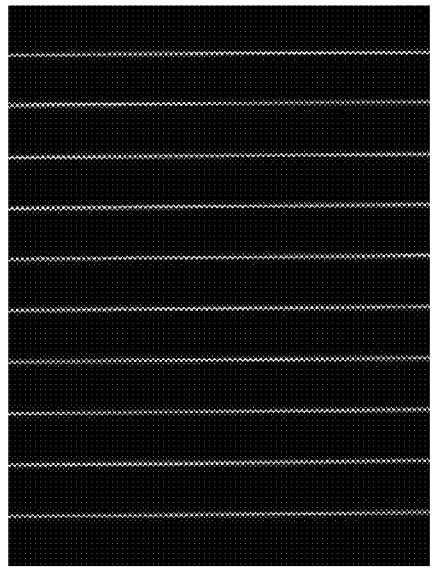
FIG. 6B is a view of a horizontal line pattern projected by the sensor.
Figure 6A:
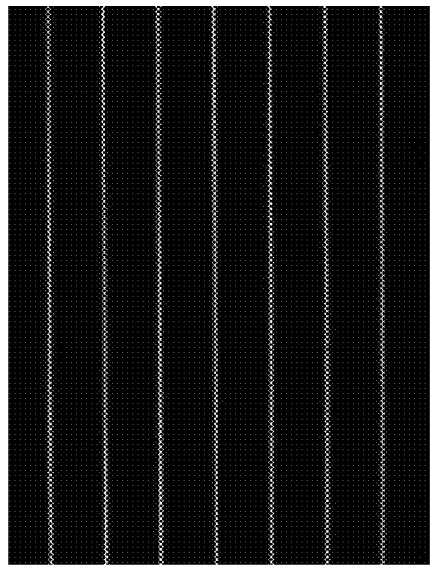
FIG. 6A is a view of a vertical line pattern projected by the sensor.
Figure 7:
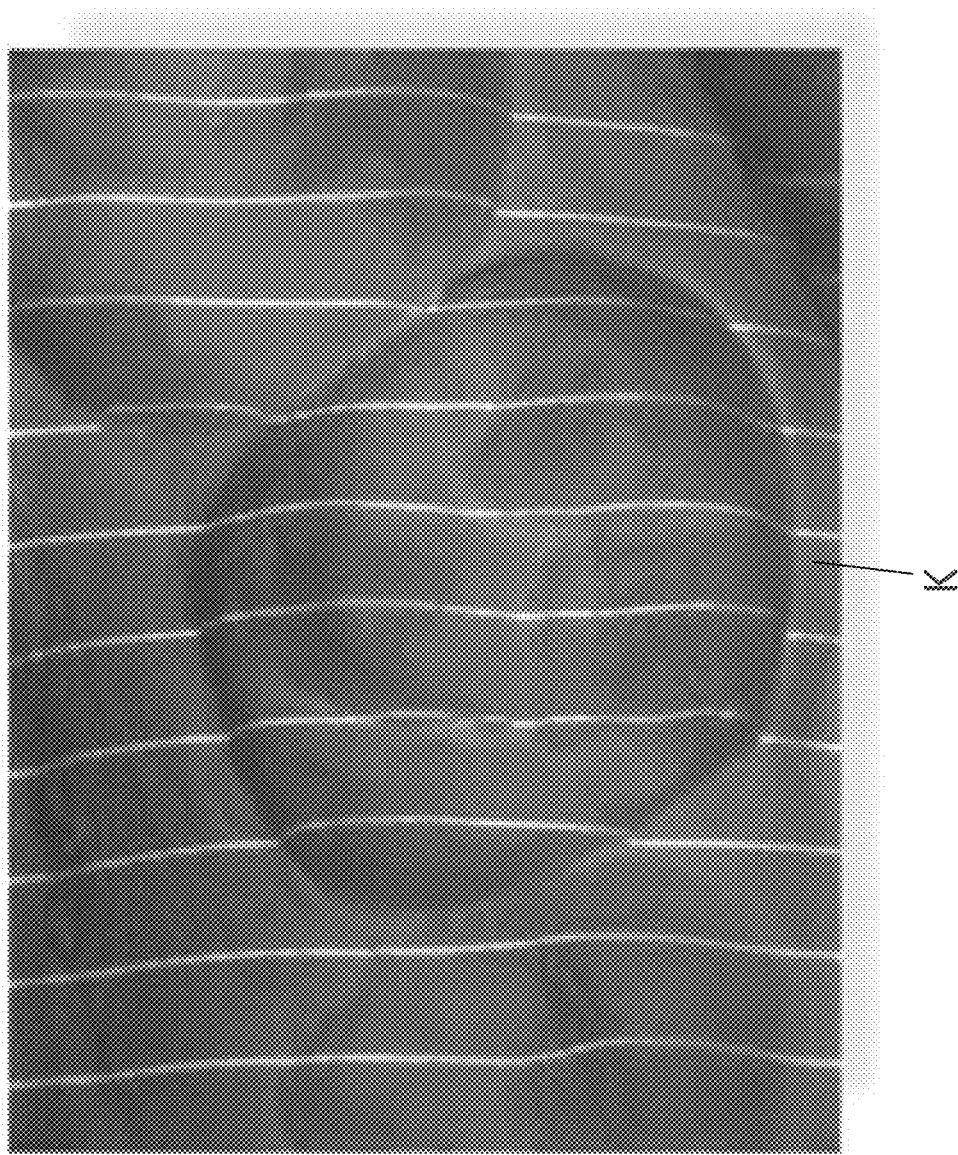
FIG. 7 shows an image generated by the camera.

An exemplary embodiment of a sensor for intraoral measurement is diagrammatically illustrated in FIG. 5. The sensor comprises a camera 1, two projectors 2 and 3, which project two mutually different patterns M1 and M2 onto the surface. Exemplary two patterns are shown in FIGS. 6A and 6B, respectively. As shown, the patterns are defined by mutually parallel, thin lines. The term "lines," as used herein, includes dashed lines, dotted lines, dash-dotted lines, and the like. Such an encoding may be helpful for the indexing of the lines, so the line distance can be narrower, without the danger of ambiguities due to wrong line indexing. The term "lines" means as well, that the width of the lines is carefully designed, in order to allow for the best localization at the video image, which is equivalent to the least measuring uncertainty. For this purpose, the line is designed to appear with a Gaussian cross section at the video target. A line which is too narrow will cause aliasing and a great amount of noise. An optimal line shape will have the width of 3-5 video pixels at the camera target. The camera views the object and the projected patterns and generates camera views K (K1, K2 ... KN). An exemplary such camera image K is shown in FIG. 7. The patterns are advantageously projected in alternation. The patterns are formed of several lines which, in the exemplary patterns are approximately parallel. The spacing distance between the lines is chosen such that the order of lines in the camera image K of the entire measuring volume is definite and clear. Reference is had to FIG. 3, in this context. The lines of the patterns M1 and M2 are perpendicular to one another. The optical axis 4 of the camera and the optical axis 5 of the projector 2 span open a triangulation plane. The optical axis 4 of the camera and the optical axis 6 of the projector 3 also span a triangulation plane. The axes of the camera and the projector enclose a respective triangulation angle θ. The angle in the exemplary embodiment is 7°. This angle is a particularly preferred selection for an intraoral dental measurement sensor. Preferably, the camera and the two projectors are disposed so as to align the triangulation planes perpendicular to one another.

Figure 8:
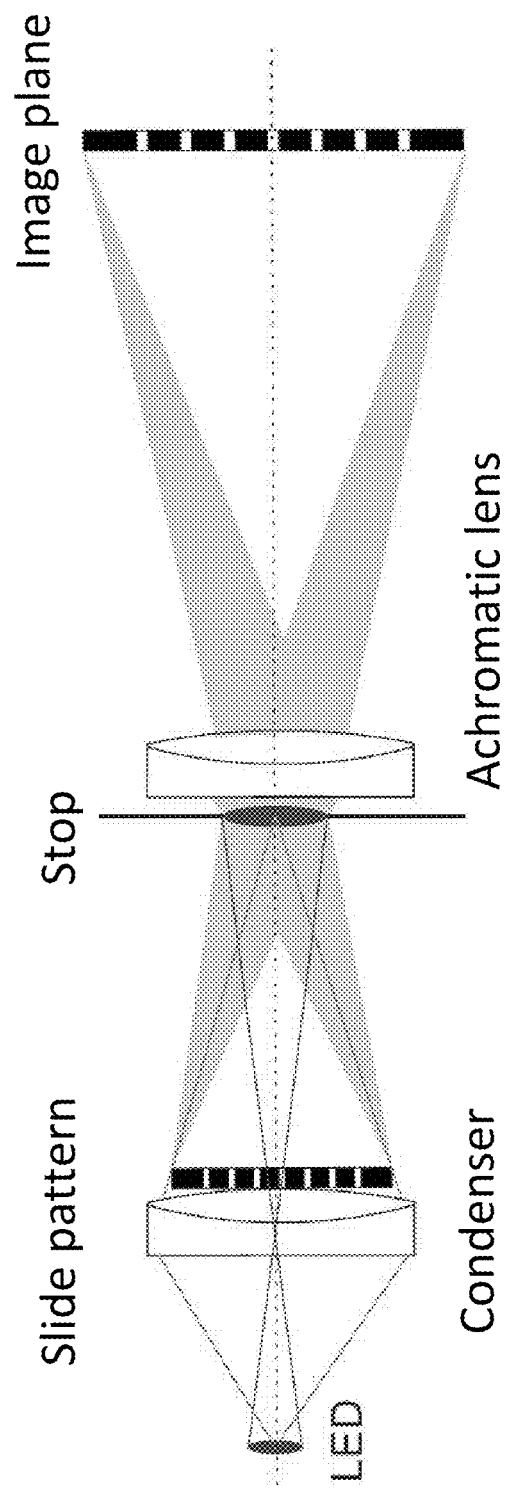
FIG. 8 is a diagrammatic side view of a slide projector.
Figure 9:
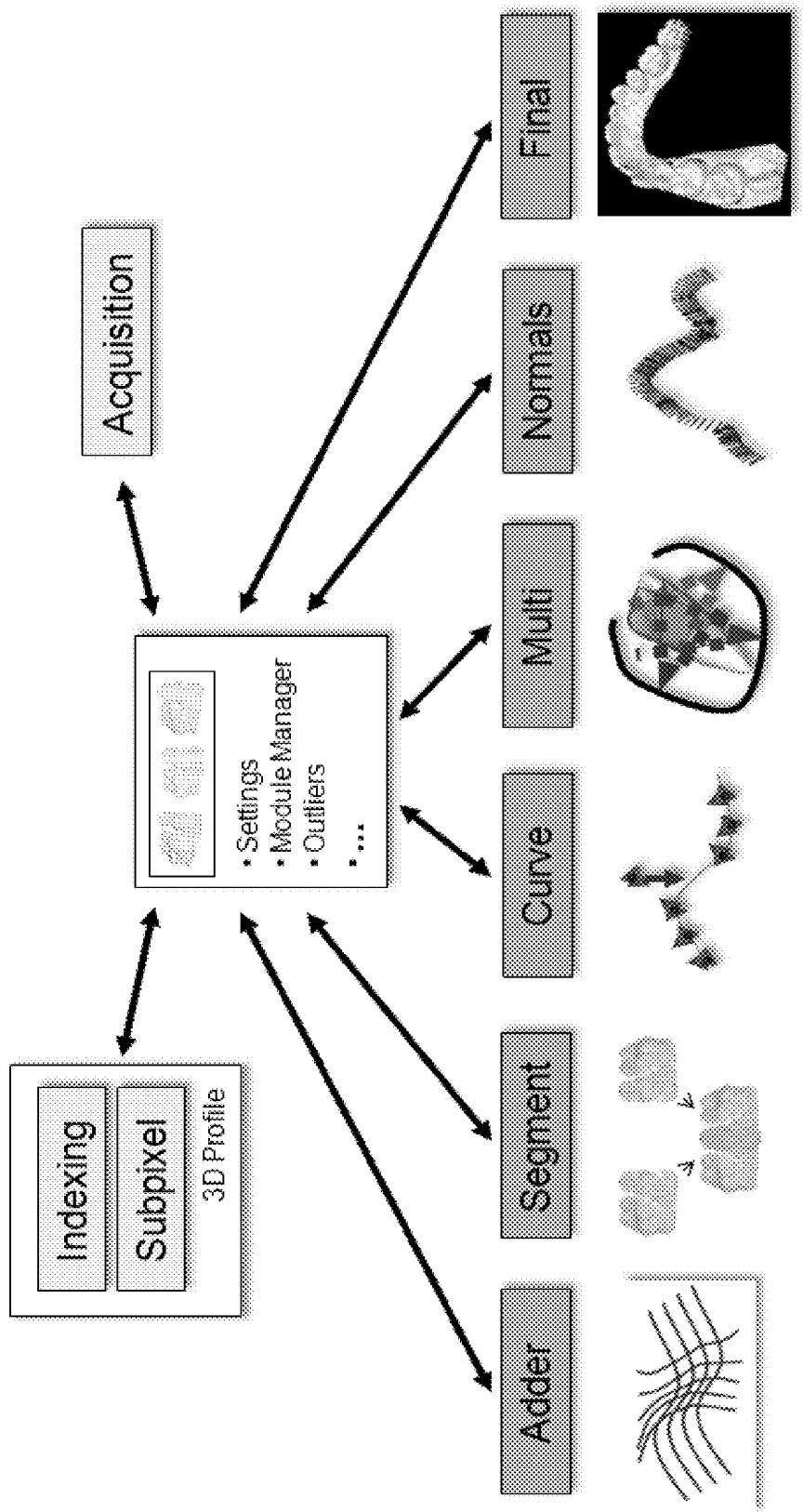
FIG. 9 is a schematic of the architecture of the capturing, registration, and visualization software.
Figure 10A:
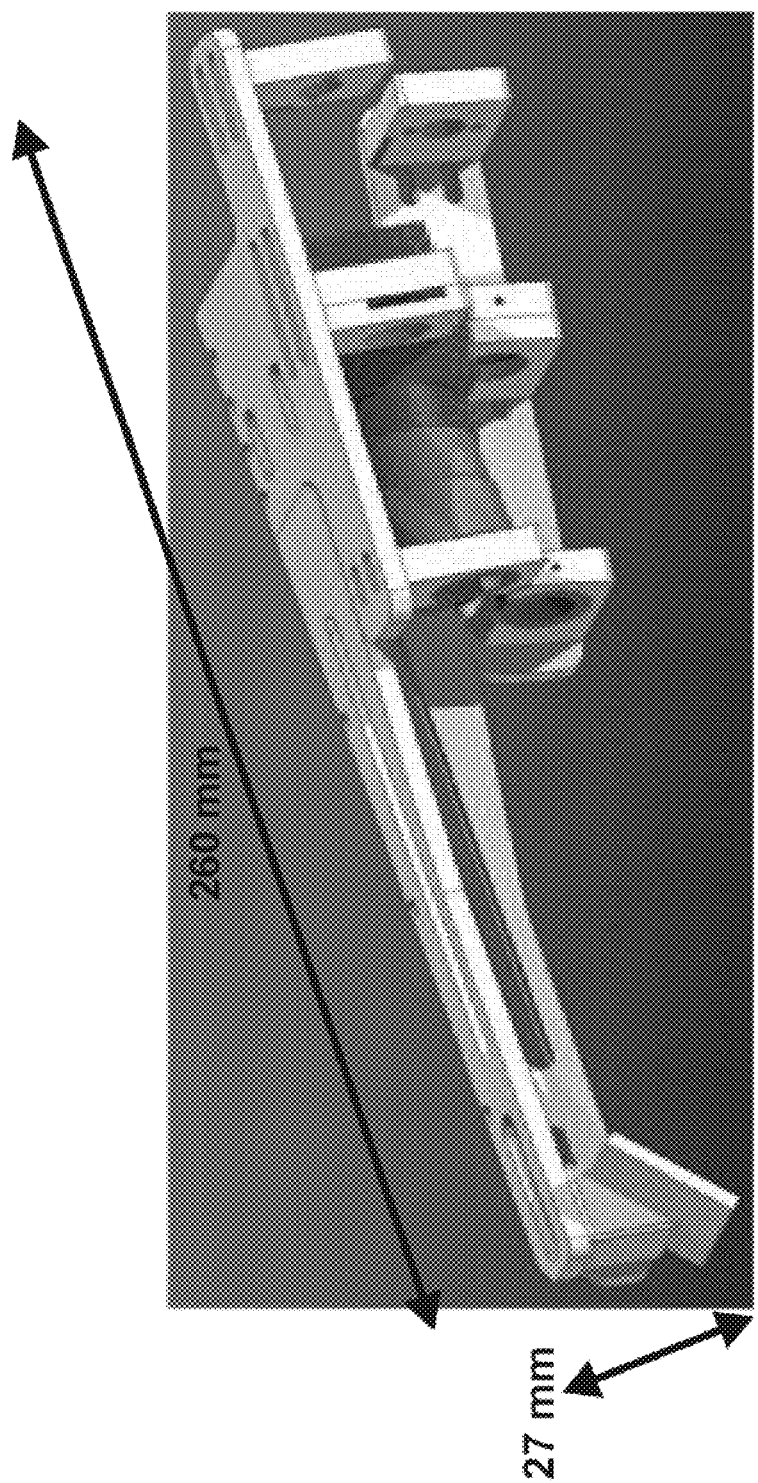
FIG. 10A is a CAD illustration of an exemplary sensor assembly.
Figure 10B:
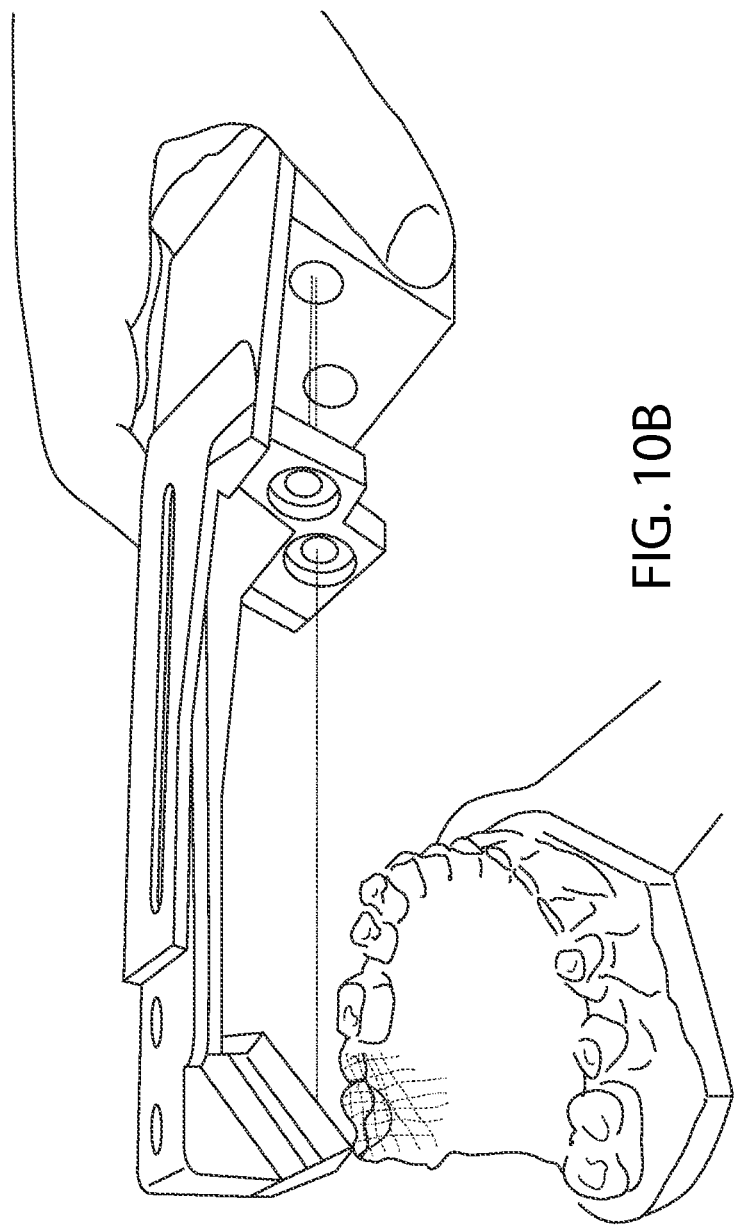
FIG. 10B is a photographic illustration of a prototype of the sensor used in a dental application.

The projectors can be produced very inexpensively and with a considerable degree of miniaturization. With reference to FIG. 8, the projectors 2 and 3 comprise a light source. This is preferably an LED or a plurality of LEDs, as indicated in the exemplary embodiment. The LED or LED array chosen in the context have a large illumination area. The light source is imaged into the pupil of the projection lens (projection achromatic lens) by way of a condenser. This is preferably done so that the pupil is completely filled. This reduces the spatial coherence and, therefore, the resulting speckle noise. The patterns M1 and M2, respectively, are formed as slide patterns, which may be produced, for example, by etched chromium on glass using a photolithographic process.

An alternative embodiment contains only a single projector with a switchable transparency, for instance, an LCD display or an FLCOS display, or a DMD display. The single projector allows the patterns M1 and M2 to be projected alternatingly. In this case, the line directions must enclose an angle of less that 45°, or −45° relative to the triangulation plane. At this time, the embodiment with two projectors is a technologically superior solution because it is more accurate, the two projectors are simpler, brighter, and less expensive.

The imaging aperture, the projection aperture, the width of the lines, as well as the observation aperture of the camera and the pixel size of the camera chip are optimized as explained above. The object is to assure that the measurement uncertainty in a single 3D view in the entire measurement volume is never greater than 30 µm (in the context of the intraoral dental measurement sensor).

The exemplary embodiment of the sensor further includes a control unit for the image acquisition, storage, and processing. Here, the control unit is a computer.

The control unit alternatingly switches the light sources of the projectors 2 and 3 for brief periods of time. The on-time is selected such that movement artifacts cannot noticeably disturb the process. Projection times of 15 ms are quite suitable for the purpose. The short projection time, shorter than the temporal spacing T between subsequent camera images, provides for higher current for limited operation as compared to continuous operation, and the attendant higher brightness. The control unit synchronizes the projectors and the camera. In the intraoral embodiment as described, T=30 ms, while the on-time is 15 ms. If it is necessary to move the sensor more quickly, a lower on-time is preferred. A faster camera frame rate can be helpful, but this is not a necessary condition.

An advantageous implementation includes the use of a system for distance or spacing detection. This should be helpful in determining whether or not the object is outside of the predetermined measurement volume of the sensor. An optical triangulation sensor or an ultrasound sensor, for instance, may serve this purpose. It is also possible, however, to deduce this information by algorithmically processing the camera images.

As repeatedly noted, the above-described exemplary embodiment is but one of many applications of the measurement principle and the concept of the invention. The concept allows easy scaling of the sensor within a very wide frame. It is possible to scale the sensor to 3D measurement of large objects, such as faces or other body parts, or even of a complete human body or other animate or inanimate objects. The parametric requirements for the sensor are determined by the specific application (e.g., working distance, measurement field, depth of the measurement space, lateral resolution, depth error, measurement time, relative motion speed between the sensor and the object, etc.) and they are easily adapted by following the above information. The parameters aperture, triangulation angle, design of the patterns M1, M2, the light source, image rate, etc. are determined as noted above.

The basic sensor principle can be easily upgraded by an option for color texture acquisition. For this purpose, one embodiment will be as follows: A color video camera or a fast still camera is mounted to the 3D sensor, at a fixed position. The field of view is the same than that of the 3D sensor. The camera is calibrated to the 3D sensor by standard procedures, so each pixel at the color camera target is connected to a light ray intersecting the measured 3D surface at a known point.

A white light source that is synchronized with the 3D sensor illuminates the object at certain intervals, for example, once in 20 frames of the 3D sensor. During the white light illumination, the line projection maybe switched off. The color images are stored and mapped onto the 3D surface data. Since the color images will look different, a smoothing of the color values will be necessary. This is a standard process, used for other optical 3D sensors with color texture, already.

The motion robustness of the sensor can be used not only for a hand held guiding. A simple way of obtaining 360° 3D data of objects is the following: the object is put onto a turntable, and while the object rotates, the sensor takes data as described above. Large objects such as cars, even rooms, can be acquired by driving the sensor on a translation stage along the object. In this case, the global error can be largely reduced, because the intrinsic accuracy is given by the translation stage, using its data of the sensor position. To finish these ideas: it is of course, possible to measure objects moving on a conveyor belt, such as cars during production.

The invention claimed is:

1. A method of acquiring surface shape information of a three-dimensional object, the method which comprises:
providing an optical sensor configured to generate three-dimensional data from a single exposure, the sensor having a first projection device, a second projection device, and a camera;
causing a relative movement between the sensor and the three-dimensional object;
projecting a first pattern having parallel lines onto the three-dimensional object with the first projection device, projecting a second pattern having parallel lines extending perpendicularly with respect to the parallel lines of the first pattern onto the three-dimensional object with the second projection device, and recording a sequence of at least partially overlapping images of the projected first and second patterns with the camera;
determining a sequence of 3D data sets from the recorded images;
performing a registration between subsequently obtained 3D data sets, and determining a surface shape of the three-dimensional object.

2. The method according to claim 1, which comprises:
determining a first 3D data set from a first image recorded by the camera immediately following the recording step;
subsequently projecting a further pattern with the projection device and recording a second image with the camera and immediately determining a second 3D data set from the second image recorded by the camera;
performing a registration between the first 3D data and the second 3D data;
subsequently recording further images and determining further 3D data, and performing registration between the further 3D data set and one or more previously acquired 3D data sets;
determining the surface shape of the three-dimensional object in real time as the sensor and the object are moved relative to one another.

3. The method according to claim 1, wherein:
the registration step is performed while causing the relative movement between the sensor and the three-dimensional object; and
the registration step includes first performing a coarse registration and then performing a fine registration.

4. The method according to claim 3, which comprises projecting the first pattern and recording an image with the camera, and subsequently projecting the second pattern and recording an image with the camera, and continuing with an alternating projection and recordation of the first and second patterns.

5. The method according to claim 4, wherein the parallel lines of the first pattern and the parallel lines of the second pattern form a sparse grid pattern.

6. The method according to claim 1, which comprises continuing the projection, recording, and registration steps on the fly to form a point cloud representing the surface shape of the object and displaying the surface shape virtually in real time.

7. The method according to claim 1, which comprises adapting a projection and exposure time period to a relative speed between the sensor and the object and to avoid a motion blur of the resulting three-dimensional data.

8. The method according to claim 1, which comprises using sparse three-dimensional data in order to avoid ambiguity and false data.

9. The method according to claim 1, which comprises:
moving the sensor along a suitable path about the object and acquiring a multiplicity of exposures, a speed of motion and a frame rate being adjusted such that adjacent pictures have significant overlap;
calculating a series of sparse 3D data of the object from the exposures;
registering each of the sets of 3D data with previously acquired 3D data sets and obtaining a substantially complete set of 3D data of the object;
displaying a representation of the 3D data to a user in real time in order to prompt the user to cover as of yet non-covered areas of the surface of the object.

10. The method according to claim 1, wherein the registration step comprises reducing and correcting registration errors by reconstructing a path of the sensor, by resection, and by finding registration errors via a deviation of the reconstructed sensor path from a smooth interpolated curve.

11. The method according to claim 1, which comprises determining whether or not an object exceeds a measurement range of the sensor by using a-priori knowledge of the object being scanned, and to correct false 3D data by an unwrapping procedure.

12. The method according to claim 1, wherein:
the first pattern is selected from the group consisting of a horizontal line pattern with a plurality of first lines extending in a given direction and a vertical line pattern with a plurality of second lines extending in a different direction traversing the plurality of first lines and defining crossing points;
the second pattern is selected from the group consisting of the horizontal line pattern with the plurality of first lines extending in the given direction and the vertical line pattern with the plurality of second lines extending in the different direction traversing the plurality of first lines and defining crossing points;
the first pattern is different from the second pattern; and
the registration step comprises using sequentially adjacent 3D data sets, one generated with the horizontal line pattern and the other with the vertical line pattern, and iteratively moving one of the 3D data sets relative to the other 3D data set until a minimum distance between all crossing points between the vertical and horizontal line patterns is reached.

13. The method according to claim 1, wherein:
said first projection device and said second projection device each have a light source, a condenser, a pattern slide, and projection optics defining an optical axis enclosing an angle with said optical axis of said camera and each defining a triangulation plane; and
said first projection device and said second projection device project mutually perpendicular patterns with a plurality of sparse lines, said camera records the projected patterns of said two projectors in alteration, and said triangulation planes defined by said camera and said two projectors, respectively, are perpendicular to one another.

14. A sensor for acquiring data representing a surface of a three-dimensional object, comprising:
a first projection device including a light source and optics for projecting a first pattern having parallel lines onto the surface of the three-dimensional object, and a second projection device including a light source and optics for projecting a second pattern having parallel lines extending perpendicularly with respect to the parallel lines of the first pattern onto the surface of the three-dimensional object;
a digital camera for recording an image of the optical pattern projected onto the surface of the three-dimensional object, said digital camera having a given optical axis;
the optical axis of said digital camera and the optical axis of said projection device enclosing a given angle and defining a triangulation plane; and
a control unit connected to and synchronizing said projection device and said digital camera and causing said camera to record a sequence of mutually overlapping images of the optical pattern sequentially projected onto the surface of the object while said sensor is moved relative to the three-dimensional object.

15. The sensor according to claim 14, wherein said digital camera is a monochromatic camera.

16. The sensor according to claim 14, wherein said first projection device and said second projection device each have a light source, a condenser, a pattern slide, and projection optics defining an optical axis enclosing an angle with said optical axis of said camera and each defining a triangulation plane.

17. The sensor according to claim 14, configured as a handheld sensor for movement about six degrees of freedom and enabling an acquisition of complex surfaces.

18. The sensor according to claim 14, which comprises an output connection enabling connection to a display device for displaying an acquisition result virtually in real time.

19. The sensor according to claim 14, which further comprises a sensor device disposed to determine whether or not an object or a portion of the object lies outside the measurement range of the sensor.

* * * * *